United States Patent
Sandul

(10) Patent No.: US 10,278,831 B2
(45) Date of Patent: May 7, 2019

(54) EXPANDABLE INTERVERTEBRAL FUSION DEVICE

(71) Applicant: Zimmer Biomet Spine, Inc., Broomfield, CO (US)

(72) Inventor: William Sandul, Broomfield, CO (US)

(73) Assignee: Zimmer Biomet Spine, Inc., Westminster, CO (US)

( * ) Notice: Subject to any disclaimer, the term of this patent is extended or adjusted under 35 U.S.C. 154(b) by 535 days.

(21) Appl. No.: 14/724,968

(22) Filed: May 29, 2015

(65) Prior Publication Data

US 2015/0374508 A1 Dec. 31, 2015

Related U.S. Application Data

(60) Provisional application No. 62/006,715, filed on Jun. 2, 2014.

(51) Int. Cl.
*A61F 2/44* (2006.01)
*A61F 2/30* (2006.01)

(52) U.S. Cl.
CPC ............ *A61F 2/4455* (2013.01); *A61F 2/447* (2013.01); *A61F 2/4425* (2013.01); *A61F 2002/30537* (2013.01); *A61F 2002/30538* (2013.01); *A61F 2002/30556* (2013.01); *A61F 2002/30601* (2013.01)

(58) Field of Classification Search
CPC ...... A61F 2/4455; A61F 2/446; A61F 2/4465; A61F 2/447; A61F 2/4425
See application file for complete search history.

(56) References Cited

U.S. PATENT DOCUMENTS

| | | | |
|---|---|---|---|
| 2006/0122701 A1* | 6/2006 | Kiester | A61F 2/447 623/17.11 |
| 2012/0059475 A1* | 3/2012 | Weiman | A61F 2/44 623/17.16 |
| 2013/0158664 A1 | 6/2013 | Palmatier et al. | |
| 2014/0094916 A1 | 4/2014 | Glerum et al. | |

(Continued)

FOREIGN PATENT DOCUMENTS

WO WO-2015187569 A1 12/2015

OTHER PUBLICATIONS

"International Application Serial No. PCT/US2015/033559, International Preliminary Report on Patentability dated Dec. 15, 2016", 9 pgs.

(Continued)

*Primary Examiner* — Si Ming Ku
(74) *Attorney, Agent, or Firm* — Schwegman Lundberg & Woessner, P.A.

(57) ABSTRACT

An expandable intervertebral fusion device is provided including a core, an upper endplate for contacting a first vertebral body and a lower endplate for contacting a second vertebral body. The expandable intervertebral fusion device is configurable in a first state, a second state and a third state. In the first state, the upper and lower endplates are generally planar to one another and define a first height. In the second state, the upper and lower endplates remain generally planar to one another and define a second height greater than the first height. In the third state, a lordotic angle is defined between the upper and lower endplates.

22 Claims, 8 Drawing Sheets

(56) References Cited

U.S. PATENT DOCUMENTS

2016/0022438 A1* 1/2016 Lamborne ............. A61F 2/4455
623/17.16

OTHER PUBLICATIONS

"International Application Serial No. PCT/US2015/033559, International Search Report dated Sep. 18, 2015", 5 pgs.
"International Application Serial No. PCT/US2015/033559, Written Opinion dated Sep. 18, 2015", 7 pgs.

* cited by examiner

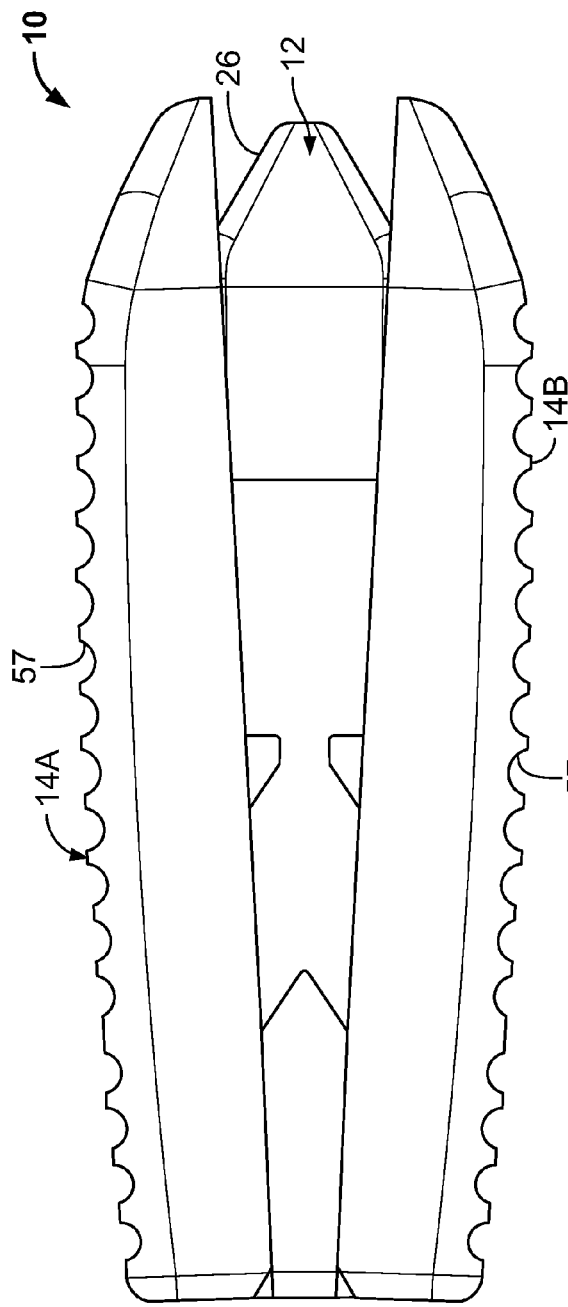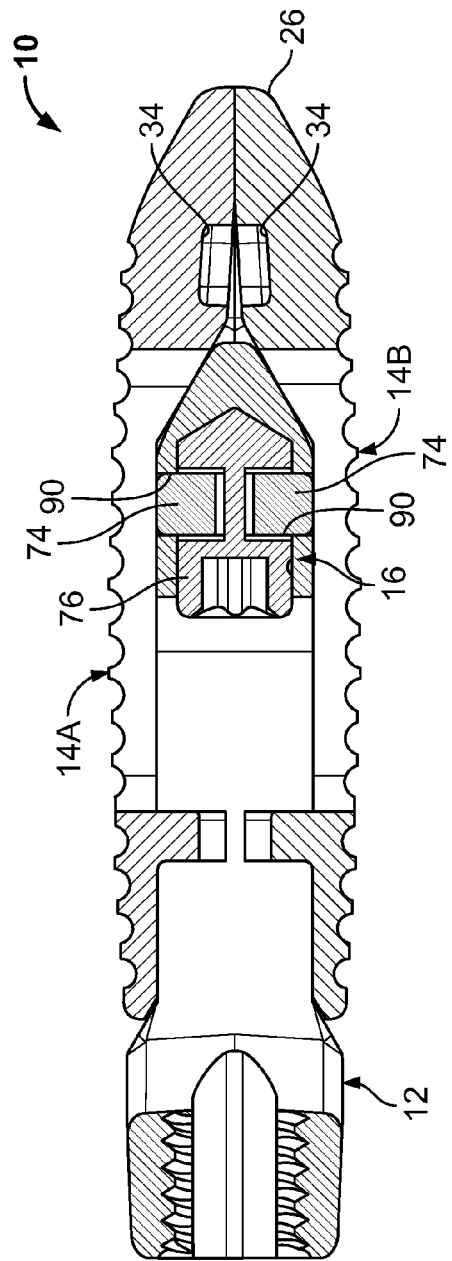

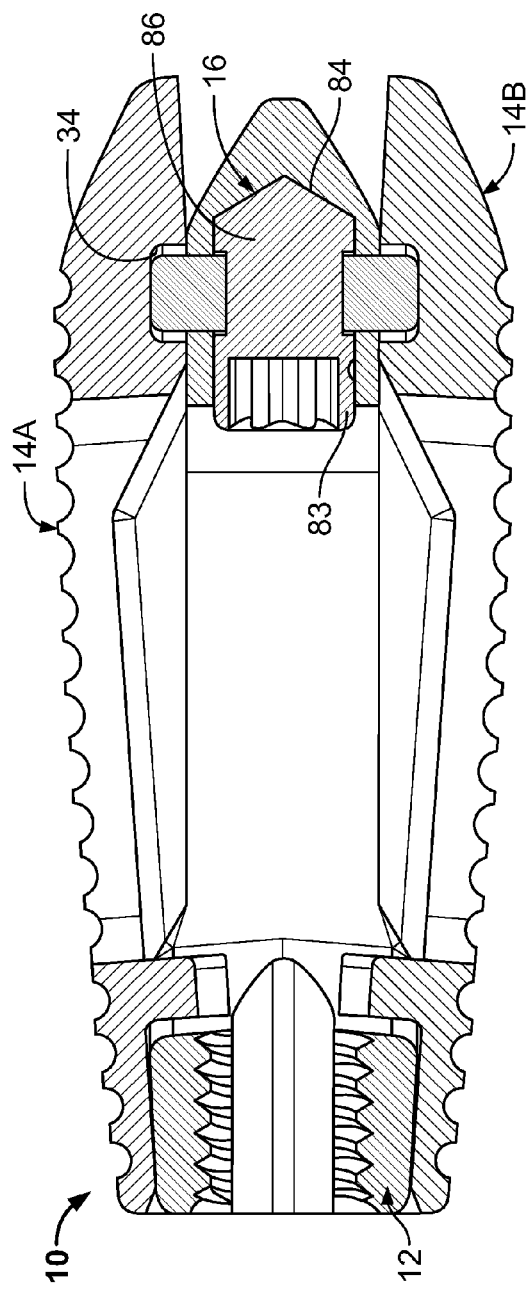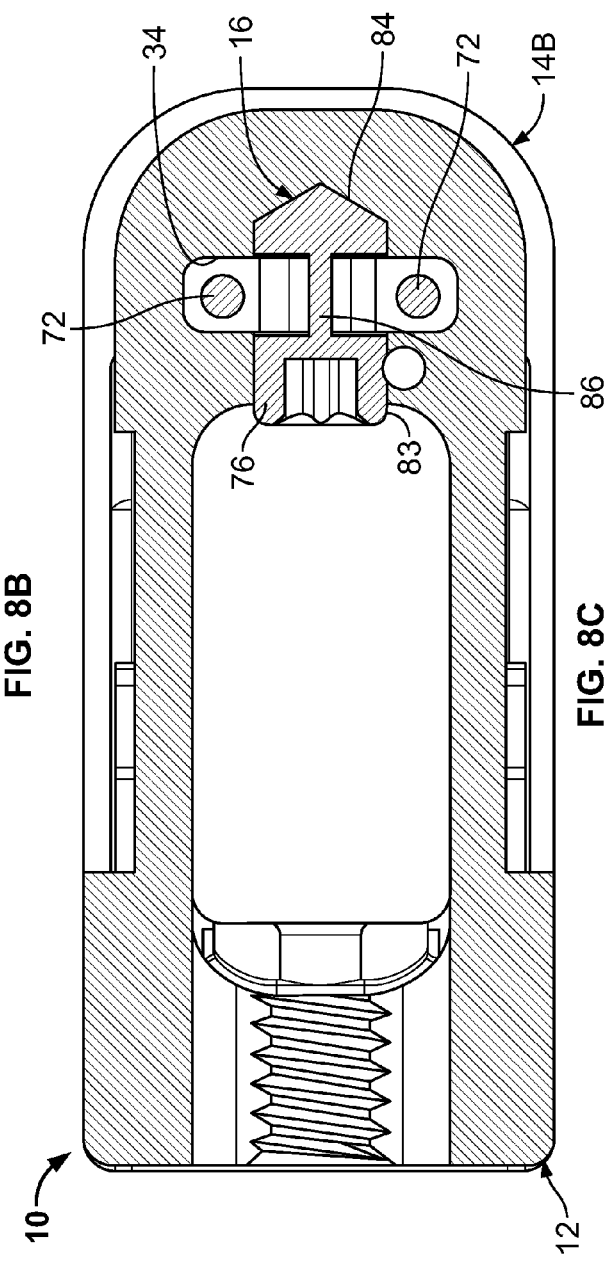

EXPANDABLE INTERVERTEBRAL FUSION DEVICE

CROSS-REFERENCE TO RELATED APPLICATIONS

This application claims the benefit of U.S. Provisional Application No. 62/006,715 filed on 2 Jun. 2014. The entire disclosure of the above application is incorporated herein by reference.

FIELD

The present teachings generally relate to a device for promoting intervertebral fusion.

BACKGROUND

This section provides background information related to the present disclosure which is not necessarily prior art.

In various orthopedic surgical procedures, it is necessary to secure portions of a spinal column in a relatively fixed relationship. This need is often a result of aging, disease, damage or congenital deformation. For example, when one or more intervertebral disks of the spine degenerates due to age, trauma or disease, the spinal cord or emergent nerve can become compressed. This condition may result in chronic and sometimes debilitating, neck, back, or peripheral pain.

One method of treatment for intervertebral disk degeneration involves surgical decompression of nerves, discectomy, and interbody fusion. Interbody fusion involves reestablishment of the normal gap between adjacent vertebral bodies. Heretofore, surgeons have employed various types of artificial implants and prostheses to stabilize the spinal column and promote fusion. The gap between adjacent vertebral bodies is commonly spanned with rigid spacer that is filled with bone graft material to facilitate bony fusion of the two vertebral bodies. A successful fusion stabilizes the spine, reduces pressure on the spinal cord and nerve roots, and reduces or eliminates back pain.

When posterior interbody fusion is performed, it is generally desirable to reduce the size of the incision to thereby facilitate patient healing. It may be challenging to insert a large enough fusion cage through the posterior access, especially when the disc space is significantly taller anteriorly than posteriorly. Limiting factors include the maximum height and width of the posterior access to the disc space.

While known devices for spinal fixation have proven to be effective in various applications to support the spinal column and promote fusion, they nevertheless can be the subject of certain improvements.

SUMMARY OF THE INVENTION

This section provides a general summary of the disclosure, and is not a comprehensive disclosure of its full scope or all of its features.

According to one particular form of the present teachings, an expandable intervertebral fusion device is provided including a core, an upper endplate for contacting a first vertebral body and a lower endplate for contacting a second vertebral body. The expandable intervertebral fusion device is configurable in a first state, a second state and a third state. In the first state, the upper and lower endplates are generally planar to one another and define a first height. In the second state, the upper and lower endplates remain generally planar to one another and define a second height greater than the first height. In the third state, a lordotic angle is defined between the upper and lower end plates.

In one particular form, the present teachings provide an expandable intervertebral fusion device including a core having a first plurality of superiorly facing inclined plane surfaces and a first plurality of inferiorly facing inclined plane surfaces. The device additionally includes a superior endplate for contacting a first vertebral body. The superior endplate includes a second plurality of inferiorly facing inclined plane surfaces for slidably engaging the first plurality of superiorly facing inclined plane surfaces of the core. The device further includes an inferior endplate for contacting a second vertebral body. The inferior endplate includes a second plurality of superiorly facing inclined plane surfaces for slidably engaging the first plurality of inferiorly facing inclined plane surfaces of the core.

In yet another particular form, the present teachings provide a method of implanting an expandable intervertebral fusion device having a core, an upper endplate and a lower endplate. The method includes implanting the device in a first state in which the upper and lower endplates are generally parallel to one another and cooperate to define a first height of the expandable intervertebral fusion device. The method additionally includes articulating the expandable intervertebral fusion device to a second state in which the upper and lower endplates remain generally parallel and cooperate to define a second height of the expandable intervertebral fusion device. The second height is greater than the first height. The method further includes articulating the expandable intervertebral fusion device to a third state in which a lordotic angle is established between the upper and lower endplates.

Further advantages of the present teachings will become more apparent below.

BACKGROUND DESCRIPTION OF THE DRAWINGS

The present invention will become more fully understood from the detailed description and the accompanying drawings, wherein:

FIG. 7C is another expandable intervertebral fusion device in a fully expanded state.

FIG. 8A is a vertebral cross sectional taken along a midline of the expandable intervertebral fusion device, the expandable intervertebral fusion device shown in an unexpanded state.

FIG. 8B is a cross section similar to FIG. 8A, the expandable intervertebral fusion device shown in an expanded state.

FIG. 8C is a horizontal cross sectional taken along a midline of the expandable intervertebral fusion device, the expandable intervertebral fusion device shown in an expanded state.

DETAILED DESCRIPTION OF VARIOUS ASPECTS

Figure 1:
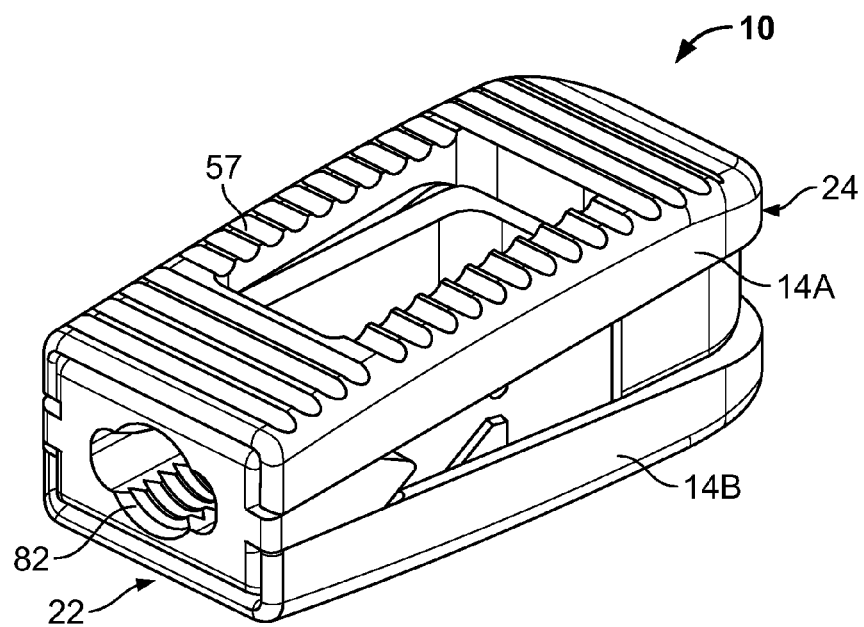
FIG. 1 is a perspective view illustrating an expandable intervertebral fusion device constructed in accordance with the present teachings.
Figure 2:
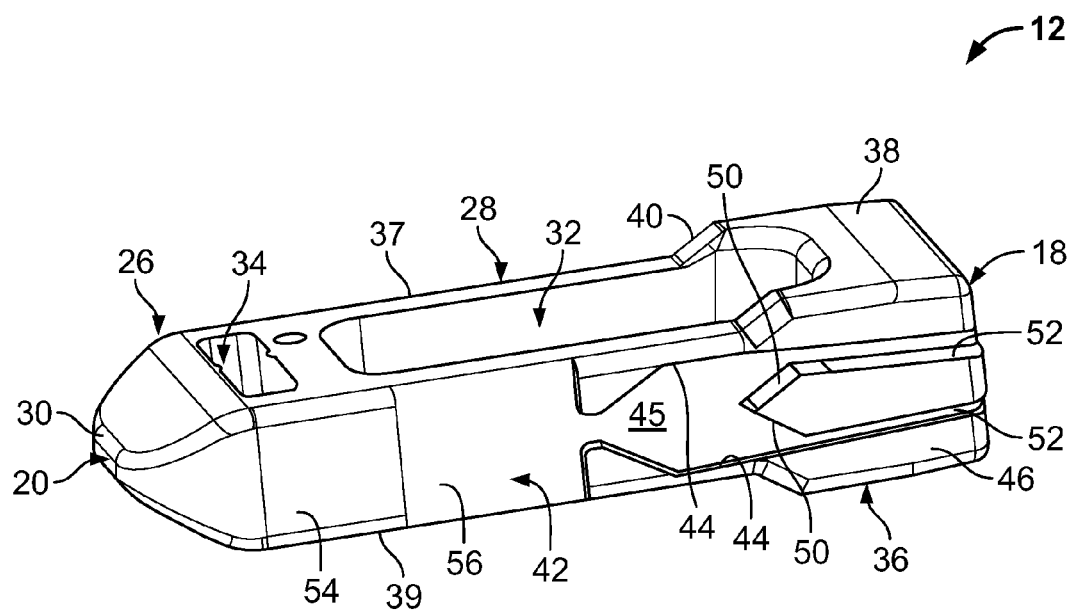
FIG. 2 is a perspective view of a core of the expandable intervertebral fusion device of FIG. 1.
Figure 3:
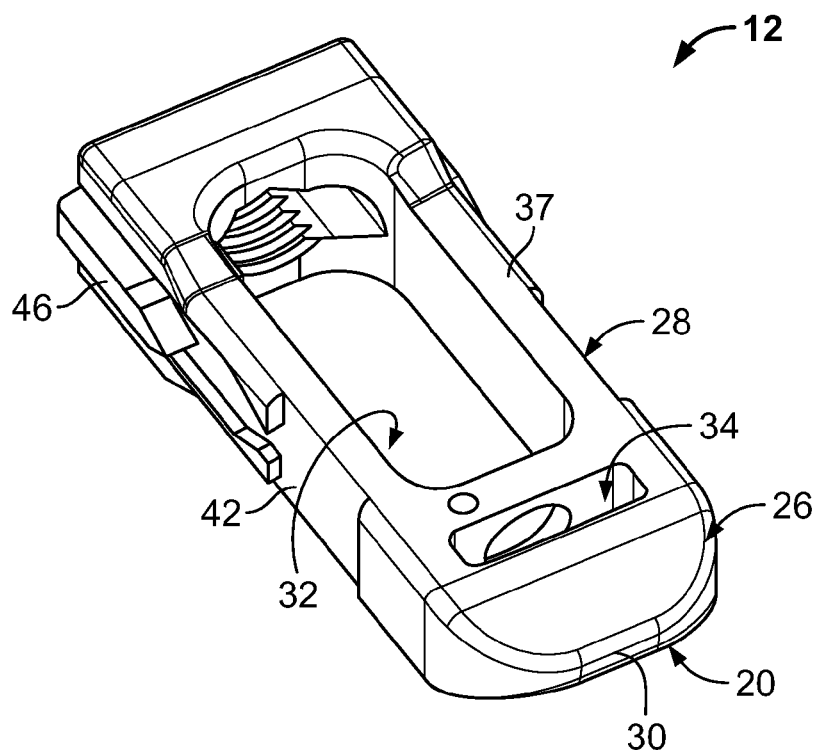
FIG. 3 is a perspective view of an alternative core of the expandable intervertebral fusion device of FIG. 1, the alternative core having a reduced height as compared to the core of FIG. 2.

Example embodiments will now be described more fully with reference to the accompanying drawings.

The following description of the preferred embodiments of the present invention is merely exemplary in nature and is in no way intended to limit the invention or its application or uses.

With general reference to FIGS. 1-8C of the drawings, an expandable intervertebral fusion device is illustrated and generally identified at reference character 10. In the embodiment illustrated, the expandable intervertebral fusion device 10 (or spinal implant) incorporates both expandable and lordosable capabilities. Those skilled in the art, however, will appreciate that the present teachings may have alternative applications within the scope of the present teachings.

In the embodiment illustrated, the expandable intervertebral fusion device 10 is shown to generally include a spacer or core 12, an upper or superior endplate 14A, a lower or inferior endplate 14B, and a locking mechanism 16. As will be appreciated further below, the core 10 and the upper and lower endplates 14A and 14B are cooperatively configured to translate relative to one another for providing an increased or expanded height to the expandable intervertebral fusion device 10. The core 12 and the upper and lower endplates 14A and 14B are also cooperatively configured to provide a lordotic angle for the expandable intervertebral fusion device.

Figure 7A:
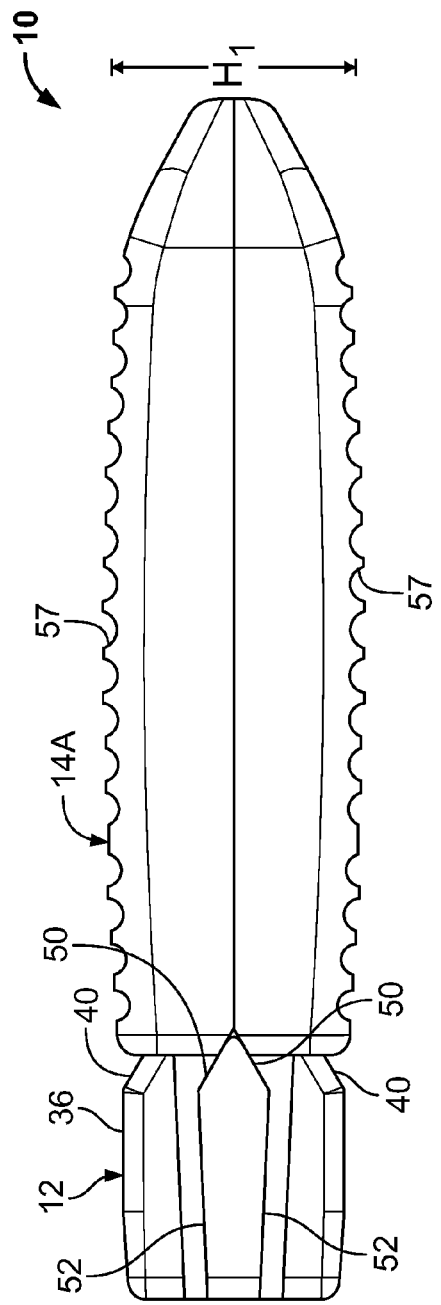
FIG. 7A is a side view of the expandable intervertebral fusion device constructed according to the present teachings, the expandable intervertebral fusion device shown in an unexpanded state.
Figure 7B:
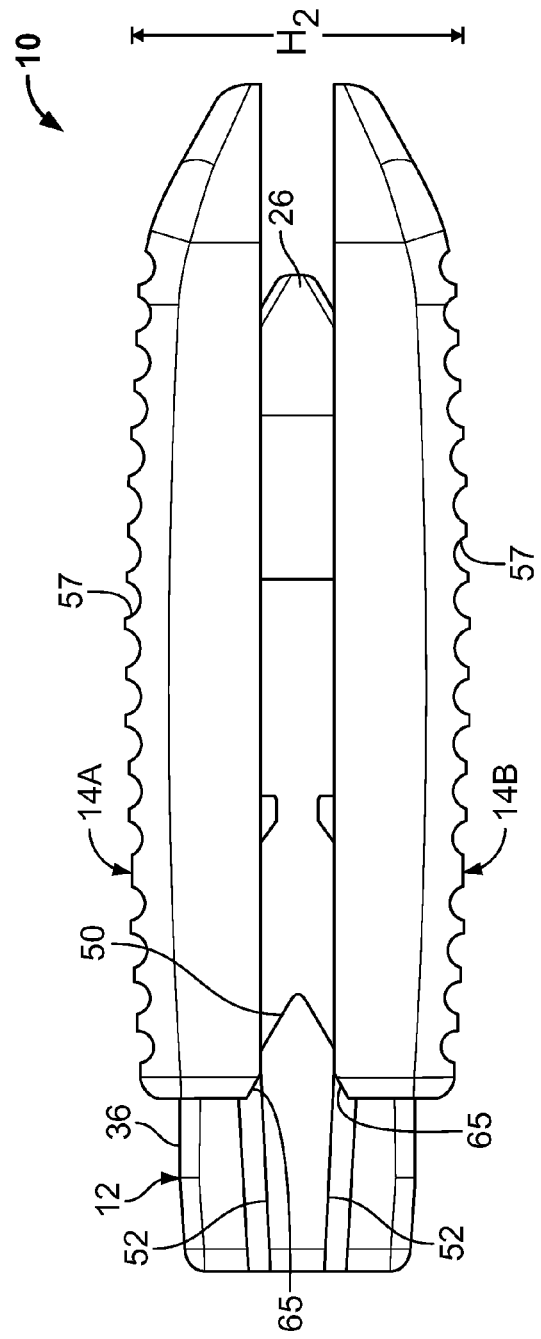
FIG. 7B is a side view of the expandable intervertebral fusion device similar to FIG. 7A, the expandable intervertebral fusion device shown in a partially expanded state.

The expandable intervertebral fusion device 10 is shown in a first state or unexpanded state intended for implantation in FIGS. 7A and 8A. In FIG. 7B, the expandable intervertebral fusion device 10 is shown in a second state or expanded state in which an unexpanded height $H_1$ of the device 10 has been increased to an expanded height $H_2$. FIGS. 1, 7C, 8B and 8C illustrate the expandable intervertebral fusion device in a third state or expanded and lordotic state. In the expanded and lordotic state, the upper and lower endplates 14A and 14B are articulate relative to one another from the parallel orientation of the expanded state such that an angle of lordosis is established between the upper and lower endplates 14A and 14B. It will be understood that in the illustrated embodiment, the second state is technically a transition state between the first and third states. This state is not sustainable in that the device 10 cannot be locked in the second state.

The core 12 of the device 10 may be generally cuboid in shape and may be a proximal or trailing end 18 and a distal or leading end 20. The device 10 correspondingly includes a proximal or trailing end 22 and a distal or leading end 24. In the embodiment illustrated, the core 12 may be constructed of polyetheretherketone or similar material. It will be appreciated, however, that alternative materials having suitable strength, durability and implantability characteristics may be used within the scope of the present teachings.

As will become more apparent below, the core 12 and the endplates 14A and 14B include corresponding inclined/declined plane surfaces. The plane surfaces cooperate to distract the endplates 14A and 14B relative to the core 12 in response to relative horizontal translations. In response to further relative horizontal translation of the core and the endplates 14A and 14B, these inclined/declined plane surfaces may cooperate to articulate the endplates 14A and 14B relative to the core 12 and thereby introduce a lordotic angle. The cooperating surfaces may be disposed both proximally and distally relative to a longitudinal axis of the device 10 for purposes of supporting the endplates 14A and 14B.

Proximate the leading end 20, the core 12 defines a forwardly tapering nose portion 26. The nose portion 26 tapers from a central portion 28 of the core 12 down to a reduced height tip 30. In the embodiment illustrated, the nose portion 26 may include upper and lower surfaces that forwardly taper. Both of the upper and lower surfaces may be disposed at an angle of about 15°-45° to the horizontal. Lateral sides of the nose portion 26 may be arcuate in a horizontal plane.

The central portion 28 of the core 12 may define one or more openings vertically extending there through. As shown, the core 12 includes a first opening 32 and a second opening 34. The first opening 32 may allow for bone graft placement and containment to facilitate intervertebral fusion. The second opening 34 may accommodate the locking mechanism 16. Upper and lower surfaces 37 and 39 of the central portion 28 of the device 10 may be generally horizontal and generally parallel to one another.

Proximate the trailing end, the core 12 includes a trailing portion 36. The trailing portion 36 may have a height greater than the height of the central portion 28. In the embodiment illustrated, upper and lower surfaces of the trailing portion 36 are substantially identical. As illustrated, the upper and lower surfaces may include a generally planar section 38 and a forwardly tapering section 40. The forwardly tapering section 40 may be on both lateral sides of the opening 32. In the embodiment illustrated, the forwardly tapering section 40 may be angled similar to the nose portion 26. In other words, the forwardly tapering section may be disposed at an angle of approximately 30° relative to the horizontal. This angle can, however, vary. The generally planar sections 38 declines (i.e., converges) slightly in a rearward direction.

As illustrated, the core 12 may include two substantially identical lateral sides 42. Each lateral side 42 may define upper and lower rails 44. The upper and lower rails 44 will be understood to be substantially identical to one another. Each rail 44 may extend from proximate the trailing end 18 of the device 10 to about a mid-point of the length of the device 10. At forward ends thereof, the rails 44 may be generally triangular in shape. Each side 42 also includes a projection 46 disposed between the rails 44. A track 45 may be defined between the rails 44.

The projection 46 forwardly extends from adjacent the trailing end 18 of the device 10. A forward end of the projection 46 includes upper and lower forwardly tapering surfaces 50 that converge to a tip. The forwardly tapering surfaces are generally aligned in a horizontal direction with the tapering section 40 of the trailing portion 36. In the embodiment illustrated, the forwardly tapering surfaces 50 are similarly angled at approximately 30° relative to the horizontal. Each projection 46 further includes upper and lower trailing surfaces 52. The upper and lower trailing surfaces 52 decline (i.e., converge) in a rearward direction. In the embodiment illustrated, the trailing surfaces 52 may decline at an angle of approximately 15° relative to the horizontal. Further in the embodiment illustrated, the trailing surfaces may be similarly angled to the generally planar sections 38. A forward section 54 of each lateral side 42 has an increased width such that a reduced width portion 56 is defined between the forward section 54 and the rails 44.

The upper and lower endplates 14A and 14B will be understood to be substantially identical. Each endplate 14A and 14B may include a bone engaging surface 57 for contacting a vertebral body. The bone engaging surfaces 57 may conventionally include a plurality of ribs 58 or other structure to prevent movement of the device 10 after implantation. With the exception of the ribs 58, the bone engaging surfaces 57 may be generally planar. As used herein, the term generally planar will encompass the slightly convex shape of the bone engaging surfaces 57 shown in the drawings. As such, it will be understood that the bone engaging surfaces 57 of the endplates 14A and 14B may be oriented generally parallel to one another. Each endplate 14A and 14B may define an opening 60 which generally aligns with the first opening 32 of the core 12 and facilitates packing of the device 10 with bone graft material.

Each endplate 14A and 14B includes a trailing end 62 and a leading end 64. As with the core 12, the endplates 14A and 14B may include a forwardly tapering nose portion 66. Each endplate 14A and 14B further includes a pair of lateral sides 68. The lateral sides 68 of the upper endplate 14A downwardly extend. Conversely, the lateral sides 68 of the lower endplate 14B upwardly extent. The lateral sides 68 are generally parallel to one another and spaced apart to accommodate a width of the core 12. Each lateral side 68 is associated with an inwardly extending rail 70. The rails 70 extend forwardly from adjacent the trailing end 62 and each have a length smaller than a corresponding length of the reduced width portion 56 of the core 12.

Figure 4A:
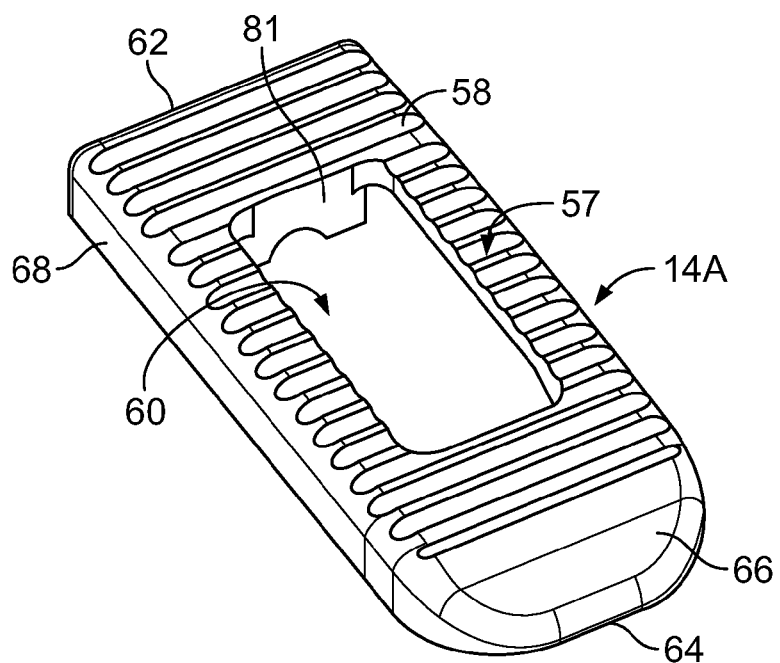
FIGS. 4A and 4B are top and bottom perspective views of an upper or superior endplate of the expandable intervertebral fusion device of FIG. 1.
Figure 4B:
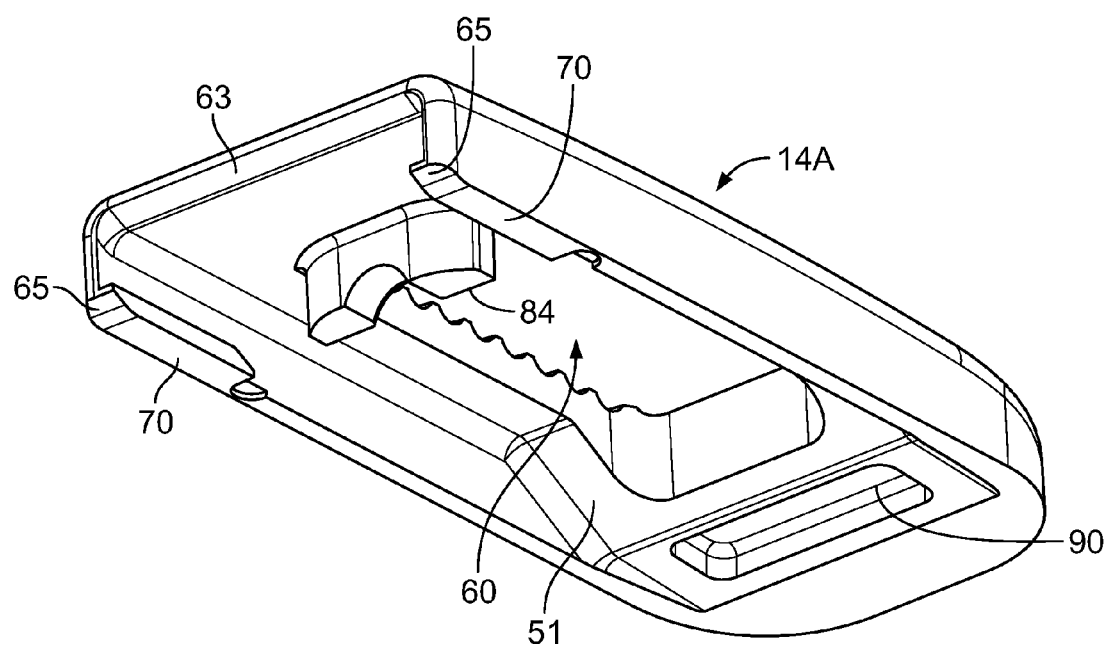
Figure 5:
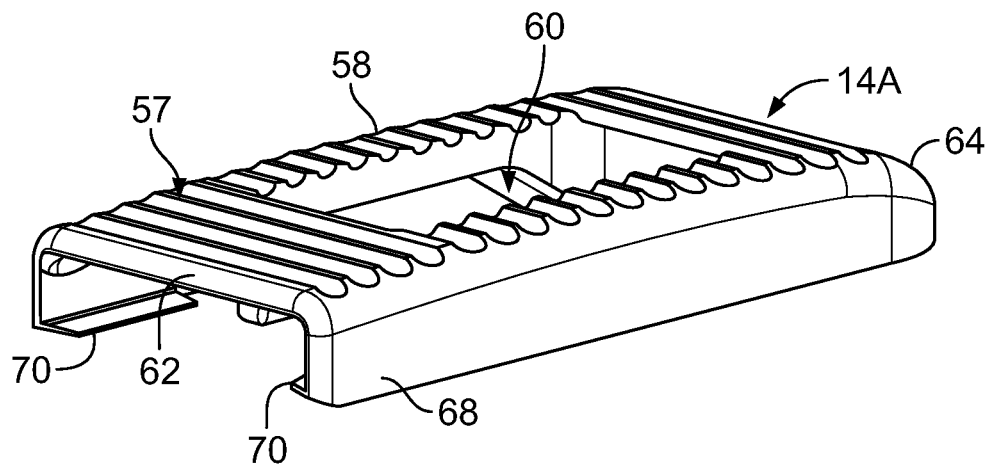
FIG. 5 is another perspective view of the upper endplate of the expandable intervertebral fusion device of FIG. 1.

As perhaps best shown in FIG. 4B, each of the upper and lower endplates 14A and 14B may include a proximally disposed chamfer. The chamfer 63 may extend across the width of the endplate 14A and 14B and may be angled similarly to the inclined surfaces of the tapering section 40 at an angle of 30° to the horizontal. Further, each rail 70 of the endplates 14A and 14B may include an angled end 65. Again, these ends 65 may be disposed at an angle of 30° to the horizontal.

The upper angled surface of the nose portion 26, the upwardly facing, tapering portion 40, and the upwardly facing, forwardly tapering surfaces 50 define a first plurality of superiorly facing inclined plane surfaces. The lower angled surface of the nose portion 26, the downwardly facing, forwardly tapering surfaces 50 and the downwardly facing tapering portion 40 define a first plurality of inferiorly facing inclined plane surfaces. The upper and lower endplates 14A and 14B include a second plurality of inferiorly facing inclined plane surfaces and a second plurality of superiorly, respectively. The second plurality of inferiorly facing inclined plane surfaces and second plurality of superiorly are defined at respective proximal ends by the chamfered surface 63 and angled ends 65 of the rails 70. The upwardly facing ones of the trailing surfaces 52 define a first plurality of superiorly facing declined surfaces for slidably engaging the superior endplate to articulate the endplate relative to the core in response to translation therebetween. The downwardly facing one of the trailing surfaces 52 define a first plurality of inferiorly facing declined plane surfaces for slidably engaging the inferior endplate to articulate the endplate relative to the core in response to translation therebetween.

The device 10 is assembled by first inserting the locking mechanism 16 in the second opening 34. Next, the upper and lower endplates 14A and 14B may be attached by vertically inserting the rails 70 into the corresponding reduced width portion 56 of the core 12. The core 12 is then forwardly translated relative to the endplates 14A and 14B such that the rails 70 are positioned between the rails 44 and in the track 45 of the core 12. As such, an axial (anteroposterior position of the endplates 14A and 14B is maintained. The fully assembled device 10 is shown in FIG. 7A, for example. In this first, or contracted or non-expanded state, the device 10 is ready for implantation. As shown in FIG. 7A, the increased height trailing portion 36 of the core 12 may be located completely rearward of the endplates 14A and 14B.

From this first state, the device 10 may be intraoperatively articulated to a second state (see FIG. 7B, for example) in which the device 10 has a second height $H_2$ which is greater than a first height $H_1$ of the device 10 in the first state. In response to this intraoperative articulation, a portion of the intervertebral space may be distracted. As shown, the endplates 14A and 14B may be generally parallel in the second state. In one application, the first height $H_1$ may be approximately 6 mm and the second height $H_2$ may be approximately 8 mm. These dimensions may range from approximately 6 mm to approximately 15 mm, however. Those skilled in the art will appreciate that these dimensions are merely exemplary and may be readily modified within the scope of the present teachings.

The device 10 may be intraoperatively articulated from the first state to the second state by horizontal translation of the endplates 14A and 14B relative to the core 12. As shown, the core 12 is translated forwardly relative to the endplates 14A and 14B from the first state to the second state. Alternatively stated, the endplates 14A and 14B may be horizontally translated rearwardly relative to the core 12.

The particular tool used to articulate the expandable intervertebral fusion device 10 will be understood to be beyond the scope of the present teachings. One tool 80 is partially shown in FIG. 6C. For purposes of translating the core 12 relative to the upper and lower endplates 14A and 14B, the tool may include a hollow shaft engaging a threaded opening 82 in the trailing end 22 of the core 12 and a rod which passes through the hollow shaft. The rod may terminate in a T-shape. As the end of the rod is inserted into the device 10, the T-shape passes below a tab 81 carried by each of the upper and lower endplates 14A and 14B. After the T-shape passes the tab, the rod may be rotated 90° and refracted for rearwardly advancing the core 12 relative to the endplates 14A and 14B.

Figure 6A:
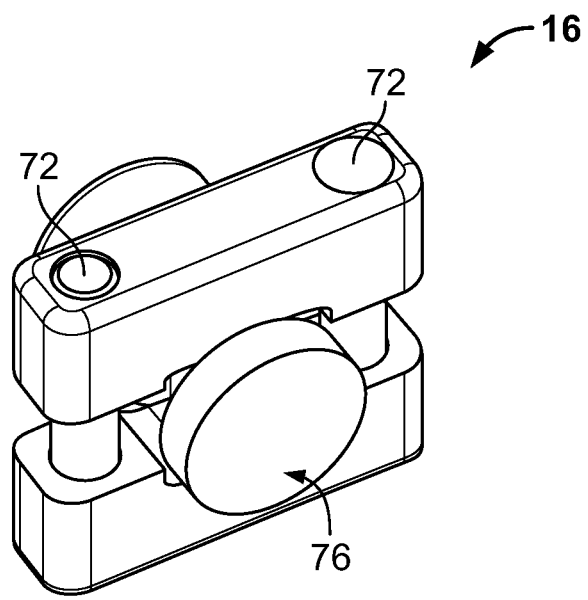
FIG. 6A is a locking mechanism of the expandable intervertebral fusion device of FIG. 1, the locking mechanism shown in an expanded or actuated state and operable to prevent relative translation between the core and the upper and lower endplates.
Figure 6B:
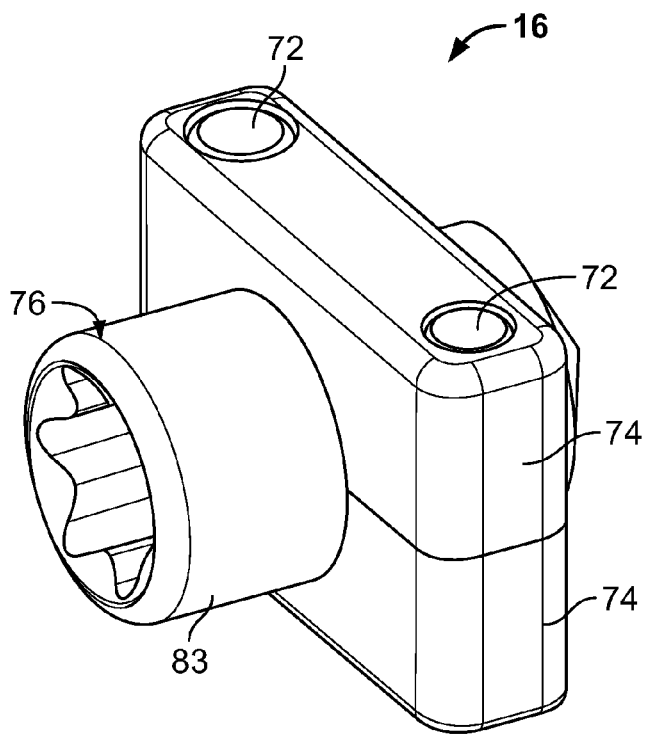
FIG. 6B is another perspective view of the locking mechanism of FIG. 6A, the locking mechanism shown in an unexpanded or non-actuated state.
Figure 6C:
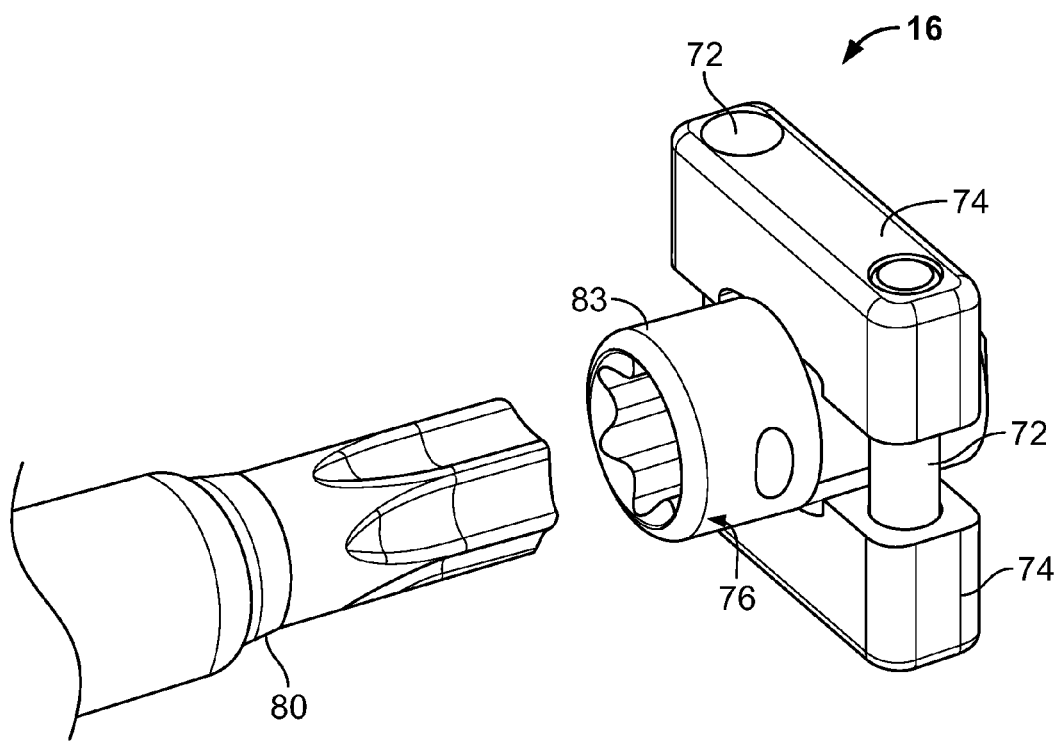
FIG. 6C is another perspective view of the locking mechanism of FIG. 6A, the locking mechanism shown in the expanded state operatively associated with a tool.

With particular reference to FIGS. 6A-6C and the cross-sectional views of FIGS. 8A-8C, the locking mechanism 16 will be further described. The locking mechanism 16 is disposed in the second opening 34 of the core 12 and carried by the core 12. The locking mechanism 16 is generally shown to include a pair of pins 72, upper and lower blocks 74 and an actuation member 76. The pins 72 allow the blocks 74 to translate relative to one another between a contracted state (as shown in FIG. 68, for example) and an expanded state (as shown in FIG. 6C, for example).

The actuation member 76 is rotatably captured between the blocks 74 and may be rotated by a tool 80 (see, FIG. 6C). The actuation member 76 may generally include a head 83, a tip 84 and a central portion 86 therebetween. The central portion 86 may be generally planar such that in a first orientation (see, FIG. 8A), the central portion 86 is horizontally oriented and the blocks 74 are in a contracted state, and in a second orientation (see, FIG. 8B), the central portion 86 is vertically oriented and the blocks 74 are in an expanded state.

As the core 12 is forwardly advanced, the nose portion 26 of the core 12 forces the leading ends 64 of the endplates 14A and 14B apart. In this regard, upper and lower facing angled surfaces of the nose portion 26 slidably engage the ramped surface 51 (see FIG. 4B) on the underside of each endplate 14A and 14B. At the same time, the tapered section 40 slide relative to the upper and lower forwardly tapering surfaces 50 of the core 12 force the trailing ends 62 of the endplates 14A and 14B apart. Also simultaneously, the tapering surfaces 50 engage angled ends 65 of the rails 70. In this manner, load is distributed between the cooperating surfaces. In the embodiment illustrated, the slopes of the nose portion 26, the tapered section 40 and the upper and lower forwardly tapering surfaces 50, the angled ends 65 of the rails 70 and the chamfer 63 are substantively identical such that the endplates 14A and 14B remain parallel in the second state. It will be appreciated that the endplates 14A and 14B are distracted in parallel directions. During this initial translation from the first state, the tapering section 40 engages the chamfered surface 63 (see FIG. 4B) on the underside of the endplates 14A and 14B.

Further forward translation of the core 12 relative to the endplates 14A and 14B serves to articulate the device 10 from the second state to a third state (see, FIG. 7C, for example) in which a lordotic angle is defined between the upper and lower endplates 14A and 14B. This lordotic angle may range from approximately 8° to approximately 12°. In the embodiment illustrated, the lordotic angle is approximately 8°. It will be understood that the lordotic angle may be changed within the scope of the present invention. During this further forward translation of the core 12 relative to the endplates 14A and 14B the rails 70 translate along the upper and lower trailing surfaces 52 and converge toward one another. At the same time, the vertical spacing of the leading ends of the endplates 14A and 14B increases by continued advancement of the nose portion 26. As a result, the lordotic angle is introduced.

In the third state, the locking mechanism 16 may be intraoperatively actuated to prevent relative translation between the core 12 and the endplates 14A and 14B. In this regard, the actuation device 76 may be rotated by the tool 80 to vertically orient the generally planar central portion 86. The blocks 74 are received within laterally extending grooves 90 defined on the inner sides of the endplates 14A and 14B.

It will now be appreciated that an expandable intervertebral fusion device is provided that allows for vertical, parallel expansion (i.e., increased device height) by way of corresponding inclined plane features between the two endplate components and the spacer component at both their proximal (back) and distal (front) ends, as they translate relative to (towards) one another in the horizontal/transverse plane. Once full vertical expansion is achieved, the incline plane features at the proximal (back) end of the spacer component transition into reverse incline (decline) plane features. The corresponding incline plane features at the distal (front) end of device, between both the endplate and spacer components, continue. As the components further translate relative to (towards) one another, the endplate components angulate, driven by the reverse incline (decline) plane features at the proximal (back) end of the spacer component and the corresponding incline plane features at the distal (front) end of the device.

The expandable intervertebral fusion device may be inserted in the same manner and using the same general surgical technique as a conventional fixed-geometry intervertebral body fusion device. However, due to its unique design for expansion, the combined expandable-lordosable device collapses (vertically) to an exceptionally low profile (e.g., 6 mm), allowing it to be more easily placed into a small or collapsed intervertebral space. It also further facilities minimally invasive surgery by way of its low initial (collapsed and nonlordotic) profile.

Spatially relative terms, such as "superior," "inferior," "lower," "upper," "proximal," "distal" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "superior" or "upper" would then be as oriented "inferior" or "lower" elements. The term "generally" as used in the terms "generally horizontal," "generally parallel" and the like shall be understood to be within ten degrees (10°) of the modified term, and preferably with five degrees (5°) of the modified term.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.2865.

What is claimed is:

1. An expandable intervertebral fusion device comprising:
   a core extending along a longitudinal axis from a distal end to a proximal end thereof, the core comprising a core nose portion extending distally from a core central portion and a threaded implantation instrument interface on the proximal end, wherein the core nose portion tapers from the core central portion down to a reduced height tip at the distal most end of the core;
   an upper endplate for contacting a first vertebral body, the upper endplate comprising a pair of lateral sides extending away from a bone engaging surface of the upper endplate; and
   a lower endplate for contacting a second vertebral body, the lower endplate comprising a pair of lateral sides extending away from a bone engaging surface of the lower endplate;
   wherein the upper endplate and the lower endplate cooperate to encapsulate the core central portion and the core nose portion in a first device state;
   wherein the core is distally advanceable along the longitudinal axis, in reference to the upper endplate and the lower endplate, to separate and urge the upper endplate and the lower endplate to a second device state where the upper and lower endplates are generally planar to one another and define a second height that is greater than the first height; and wherein the core is further distally advanceable along the longitudinal axis to urge the upper endplate and the lower endplate to a third device state wherein the upper endplate and the lower endplate cooperate to define a lordotic angle.

2. The expandable intervertebral fusion device of claim 1, wherein the expandable intervertebral fusion device is intraoperatively adjustable between the first, second, and third device states.

3. The expandable intervertebral fusion device of claim 1, wherein the core further comprises a trailing portion extending proximally from the core central portion, wherein the trailing portion comprises a height that is greater than the height of the core central portion.

4. The expandable intervertebral fusion device of claim 3, wherein the trailing portion is proximal to the upper endplate and the lower endplate in the first device state.

5. The expandable intervertebral fusion device of claim 4, wherein distal advancement of the core portion along the longitudinal axis urges the trailing portion in between the upper endplate and the lower endplate.

6. The expandable intervertebral fusion device of claim 1, wherein:
the core includes a first plurality of superiorly facing inclined plane surfaces and a first plurality of inferiorly facing inclined plane surfaces;
the upper endplate includes a second plurality of inferiorly facing inclined plane surfaces for slidably engaging the first plurality of superiorly facing inclined plane surfaces; and
the lower endplate includes a second plurality of superiorly facing inclined plane surfaces for slidably engaging the first plurality of inferiorly facing inclined plane surfaces.

7. The expandable intervertebral fusion device of claim 6, wherein each inclined plane surface of the first and second pluralities of superiorly facing inclined plane surfaces and the first and second pluralities of inferiorly facing inclined plane surfaces is disposed at a common angle relative to a horizontal axis extending from a proximal end to a distal end of the core.

8. The expandable intervertebral fusion device of claim 1, further comprising a locking mechanism engageable to prevent translation of the core relative to the upper endplate and the lower endplate in the third device state.

9. The expandable intervertebral fusion device of claim 1, wherein the core further comprises a first opening disposed therein for receiving bone graft material.

10. An expandable intervertebral fusion device, comprising:
a core extending along a longitudinal axis from a distal end to a proximal end thereof, the core comprising a core nose portion extending distally from a core central portion to the distal end where the core nose portion tapers down to a reduced height tip, a first plurality of superiorly facing inclined plane surfaces, a first plurality of inferiorly facing inclined plane surfaces, and a implantation instrument interface on the proximal end;
a superior endplate for contacting a first vertebral body, the superior endplate comprising a second plurality of inferiorly facing inclined plane surfaces for slidably engaging the first plurality of superiorly facing inclined plane surfaces of the core, a pair of lateral sides extending away from a bone engaging surface of the superior endplate, and a forwardly-tapering endplate nose portion; and
an inferior endplate for contacting a second vertebral body, the inferior endplate comprising a second plurality of superiorly facing inclined plane surfaces for slidably engaging the first plurality of inferiorly facing inclined plane surfaces of the core, a pair of lateral sides extending away from a bone engaging surface of the lower endplate, and a forwardly-tapering endplate nose portion;
wherein the upper endplate and the lower endplate cooperate to encapsulate the core central portion and the core nose portion in a first device state where the upper and lower endplates are generally planar to one another and define a first height;
wherein the core is distally advanceable along the longitudinal axis to separate and urge the upper endplate and the lower endplate to a second device state where the upper and lower endplates are generally planar to one another and define a second height that is greater than the first height; and
wherein the core is further distally advanceable along the longitudinal axis to urge the upper endplate and the lower endplate to a third device state wherein the upper endplate and the lower endplate cooperate to define a lordotic angle.

11. The expandable intervertebral fusion device of claim 10, wherein the first plurality of superiorly facing inclined plane surfaces cooperate with the second plurality of inferiorly facing inclined plane surfaces to superiorly distract the superior endplate and the first plurality of inferiorly facing inclined plane surfaces cooperate with the second plurality of superiorly facing inclined surfaces to inferiorly distract the inferior endplate.

12. The expandable intervertebral fusion device of claim 11, wherein the expandable intervertebral fusion device is intraoperatively adjustable between the first, second, and third device states.

13. The expandable intervertebral fusion device of claim 10, wherein the first plurality of superiorly facing inclined plane surfaces comprises at least a first superiorly facing inclined plane surface defined by the core nose portion of the core and a second superiorly facing inclined plane surface defined by a trailing portion of the core.

14. The expandable intervertebral fusion device of claim 10, wherein each inclined plane surface of the first and second pluralities of superiorly facing inclined plane surfaces and the first and second pluralities of inferiorly facing inclined plane surfaces is disposed at a common angle relative to the longitudinal axis.

15. The expandable intervertebral fusion device of claim 10, wherein the core further comprises a first plurality of superiorly facing declined surfaces for slidably engaging the superior endplate to rotate the superior endplate relative to the core when the core is distally advanced to urge the upper endplate and the lower endplate from the second device state to the third device state.

16. The expandable intervertebral fusion device of claim 10, wherein the core comprises a first plurality of superiorly facing declined plane surfaces and the core further comprises a first plurality of inferiorly facing declined surfaces for slidably engaging the inferior endplate to rotate the inferior endplate relative to the core when the core is distally advanced to urge the upper endplate and the lower endplate from the second device state to the third device state.

17. The expandable intervertebral fusion device of claim 10, further comprising a locking mechanism disposed within an opening in the core, the locking mechanism engageable to prevent translation of the core relative to the upper endplate and lower endplate in the third device state.

18. A method of implanting an expandable intervertebral fusion device having a core, an upper endplate and a lower endplate, the method comprising:

engaging a proximal end of the core of the expandable intervertebral fusion device with an implantation instrument;

implanting the expandable intervertebral fusion device in a first device state in which the upper and the lower endplates are generally parallel to one another, cooperate to encapsulate a central portion and a nose portion of the core, and cooperate to define a first height, wherein the core nose portion tapers from the core central portion down to a reduced height tip at the distal most end of the core;

distally advancing the core distally along a longitudinal axis thereof, relative to the upper and the lower endplates, to separate and urge the upper endplate and the lower endplate to a second device state in which the upper and lower endplates remain generally parallel and cooperate to define a second height of the expandable intervertebral fusion device; the second height being greater than the first height; and further distally advancing the core along the longitudinal axis to urge the upper endplate and the lower endplate to a third device state in which a lordotic angle is established between the upper and lower endplates.

19. The method of implanting an expandable intervertebral fusion device of claim 18, wherein distally advancing the core along the longitudinal axis to urge the upper endplate and the lower endplate to a second device state further comprises urging a trailing portion of the core from a position proximal to the upper endplate and the lower endplate in the first device state to a position at least partially in between the upper endplate and the lower endplate.

20. The method of implanting an expandable intervertebral fusion device of claim 18, further comprising engaging a threaded distal end of the core with a hollow shaft prior to distally advancing the core.

21. The method of implanting an expandable intervertebral fusion device of claim 18, further comprising engaging a locking mechanism to prevent translation of the core relative to the upper endplate and the lower endplate in the third device state.

22. The expandable intervertebral fusion device of claim 9, wherein the core further comprises a second opening disposed therein for receiving a locking device.

* * * * *